United States Patent [19]

Kawai et al.

[11] 4,065,358

[45] Dec. 27, 1977

[54] APPARATUS FOR PRODUCING REACTIONS IN COLORIMETRIC CELLS

[75] Inventors: Shoji Kawai; Kenichi Nishimura, both of Kyoto; Mitsuo Fukuda, Ibaragi, all of Japan

[73] Assignee: Kabushiki Kaisha Kyoto Daiichi Kagaku, Japan

[21] Appl. No.: 684,918

[22] Filed: May 10, 1976

[30] Foreign Application Priority Data

May 17, 1975 Japan .................................. 50-58847

[51] Int. Cl.² ............................................. C12K 1/10
[52] U.S. Cl. ............................. 195/127; 195/103.5 R; 23/259; 23/292
[58] Field of Search ............. 195/103.5 R, 127, 103.7; 23/259, 292

[56] References Cited

U.S. PATENT DOCUMENTS

| | | | |
|---|---|---|---|
| 2,699,378 | 1/1955 | Koelle | 23/292 |
| 3,733,179 | 5/1973 | Guehler | 23/259 |
| 3,768,979 | 10/1973 | Mead et al. | 23/259 |

Primary Examiner—Alvin E. Tanenholtz
Attorney, Agent, or Firm—Steinberg & Blake

[57] ABSTRACT

An apparatus according to which a sample and a reagent are mixed together at a given temperature in a colorimetric cell to enable a property of the sample to be determined in an instrument such as a photoelectric colorimeter or a spectrophotometer. The sample and reagent are initially situated in a pair of containers one of which can be enclosed entirely within the other with the inner container extending above the level of the contents in the outer container. A colorimetric cell is connected in a fluid-tight manner at its open end to an upper open top of the outer container, and then after the entire assembly and the contents of the containers are brought to a given temperature, this assembly is inverted to discharge the contents of both containers into the colorimetric cell. Then, by situating the latter cell in an instrument of the above type it is possible to direct through the cell and the contents therein light of a given wavelength which will be absorbed by a component of the reagent in a manner which will indicate a property of the sample.

15 Claims, 11 Drawing Figures

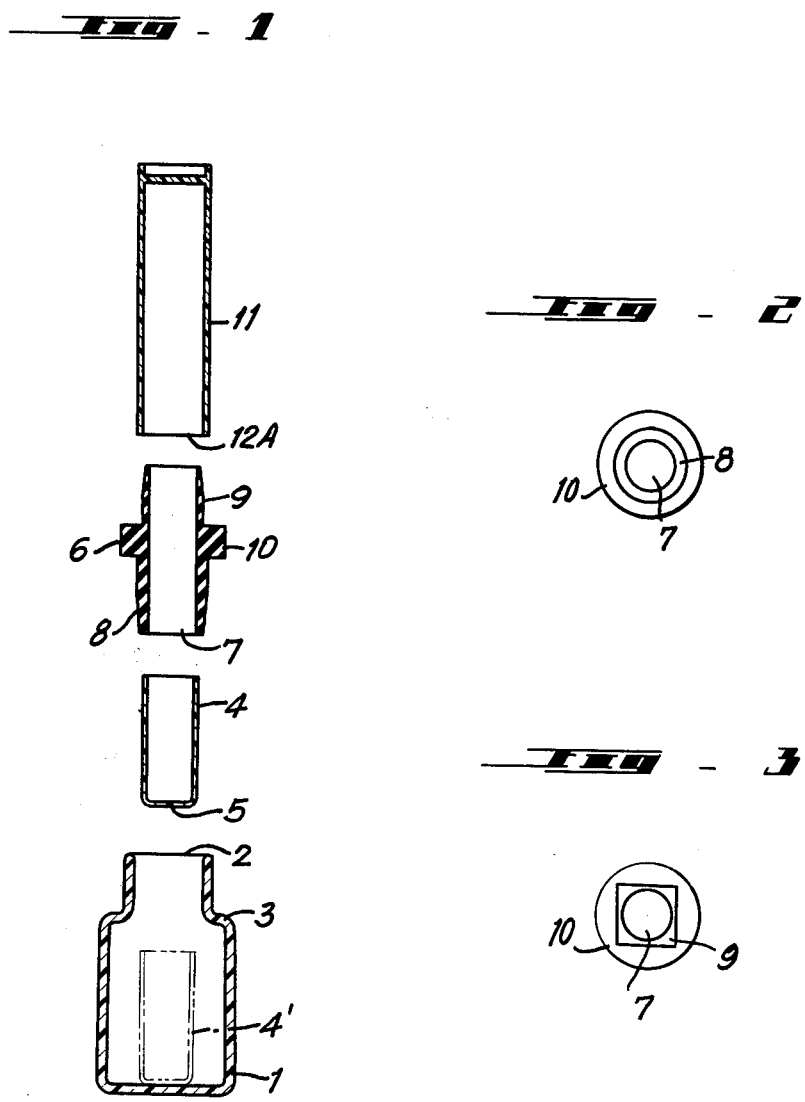

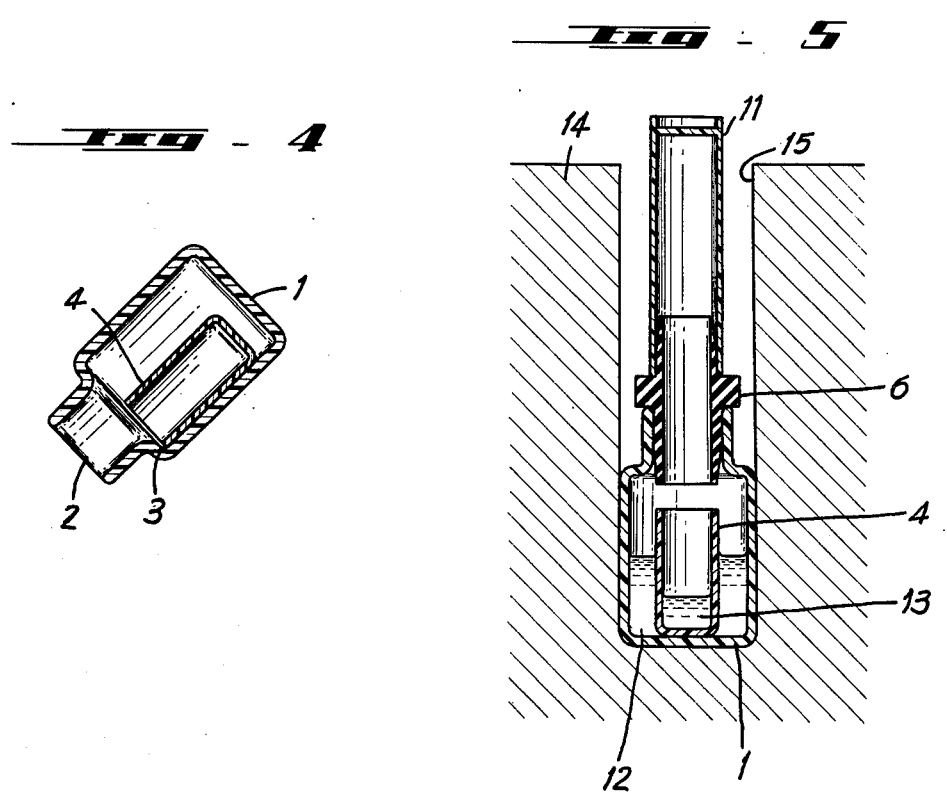

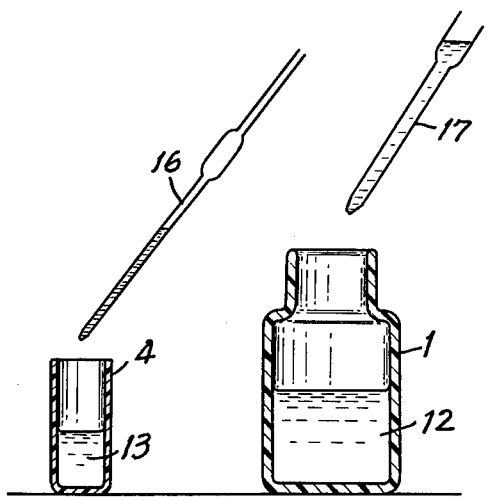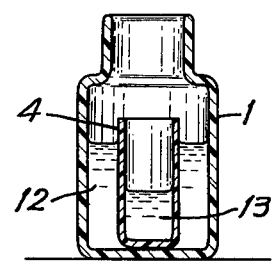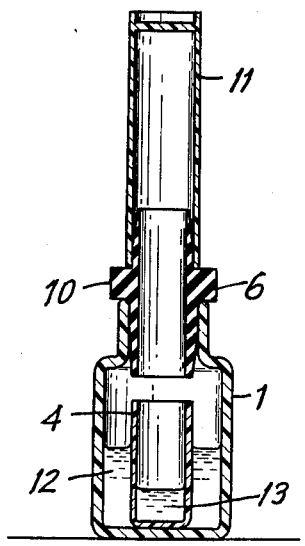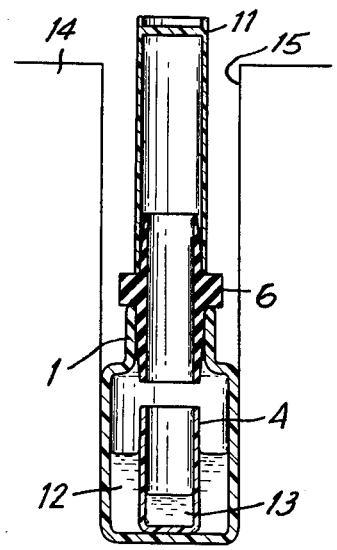

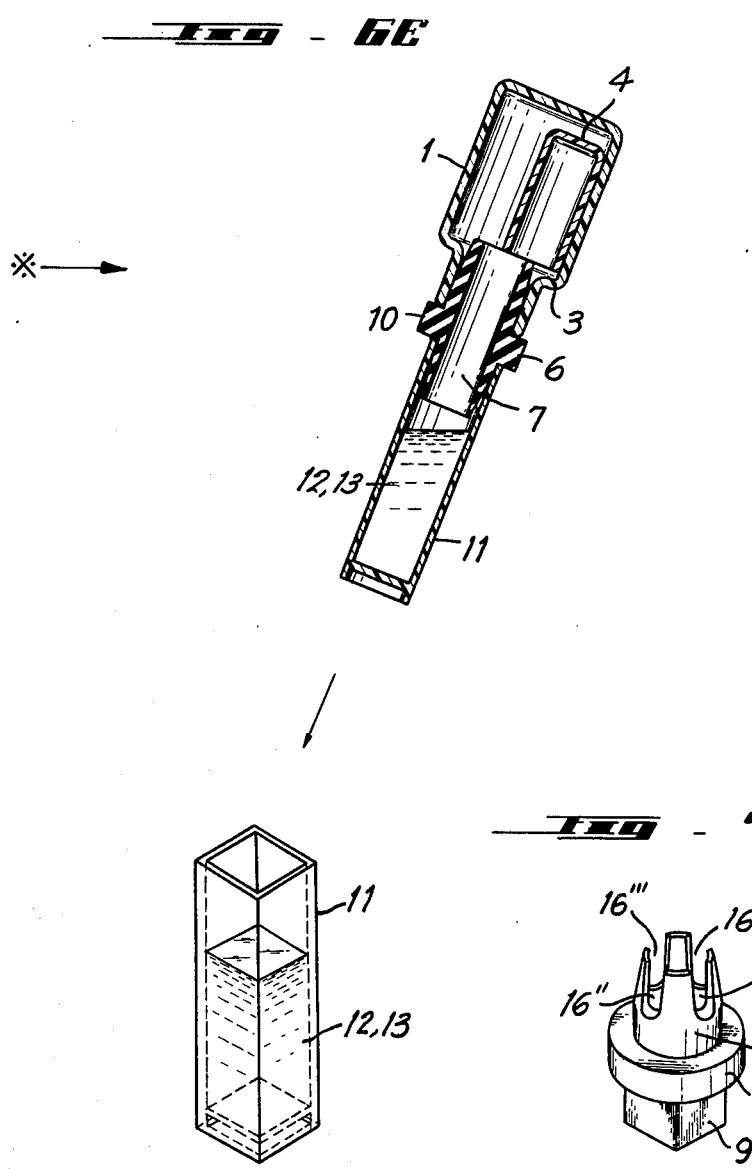

APPARATUS FOR PRODUCING REACTIONS IN COLORIMETRIC CELLS

BACKGROUND OF THE INVENTION

The present invention relates to apparatus for determining a property of a sample such as an enzyme sample. For example, the present invention may be used to determine the enzyme activity of the sample.

In connection with methods and apparatus for determining properties of the above type, various problems are encountered at the present time. In order to illustrate the problem solved by the present invention, the following example of enzyme activity value measurement may be considered.

The following reaction formula represents, for example, the reaction of activity value measurement of LDH (lactate dehydrogenase) which in a suitable serum forms a sample which is to be tested. LDH acts as a catalyzer for the reaction in the direction of the arrow:

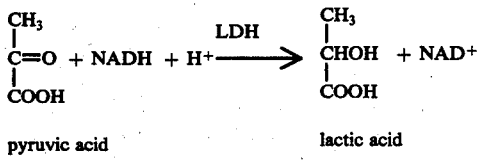

pyruvic acid    lactic acid

While the actual reaction set forth above is reversible, in the case where use is made of a reagent containing pyruvic acid as a substrate and NADH as a coenzyme, the reaction equilibrium is directed in a pronounced manner toward the right, and during the initial time period when the reaction takes place, NADH is consumed in a rate-determining state so that the concentration of NADH diminishes at a constant rate. It is thus possible to measure the concentration of this NADH by measuring the extent to which ultraviolet light of a wavelength of, for example, 340 nm (nanometer) is absorbed when directed through the mixture of the sample and reagent while the above reaction is going forward. Thus the enzyme activity value can be represented by the rate of consumption or in other words the rate at which the concentration of NADH diminishes, which is to say the rate variation of absorbance of the light of the above wavelength with respect to time.

Thus, it is important that the real value of enzyme activity correspond to the variation of the light absorbance as set forth above.

Thus, with the present invention it is possible to provide for measurement of an enzyme activity value by way of a photoelectric colorimeter or a spectrophotometer, and in particular the present invention relates to reaction containers to bring about accurate control of the enzyme reaction temperature.

The possibility of measuring enzyme activity by utilizing ultraviolet light absorption by the coenzyme NADH has greatly advanced clinical biochemical examination and has greatly improved the technique of medical examination and treatment.

This enzyme activity value measuring method is characterized in that the reaction rate between a chemical substance forming a substrate and an enzyme which has a specific catalyzing action on the substrate can be directly and optically observed. In this way it has become possible to measure enzyme activity values according to a uniform method and in a rapid manner with respect to very many types of enzymes.

In practice, however, this kinetic assay method has various problems so that it cannot be readily adopted by many clinical examiners.

One of the problems is with respect to the time restriction of the rate-determining step measured only in the rate-determining state during the initial period of the reaction. The real value cannot be obtained if, as the reaction advances to the right with lapse of time, the reaction in the reversed direction commences or a reaction-alienated substance is produced. Moreover, the enzyme activity is influenced to a very high degree by temperature. For example, in the vicinity of 30° C, it has a temperature gradient of 7% per 1° C, so that for accurate measurement an extremely elaborate temperature control is required. Thus, in connection with enzyme activity value measurement, all of the elements constituting the reaction system must be controlled so as to have the predetermined temperature up to the time of initiation of the reaction, and after initiation of the reaction the temperature of the reaction system must be kept at a predetermined value until the measurement is completed.

In practice, however, this latter type of procedure is extremely difficult to achieve. For example, if the serum sample, the substrate and the NADH solution are separately heated until they reach the predetermined temperature, the temperature of the reaction system may be remarkably different from the predetermined value as a result of loss of heat caused through measurement by pipette, mixing, transfer to the absorption cell, etc.

In order to avoid difficulties of the above type, it has been proposed to compensate the measurement value with respect to the temperature at the time of reaction. Clinically, however, such procedures never result in reliable values due to the nature of the enzyme which is generally composed of several isomers.

SUMMARY OF THE INVENTION

It is accordingly a primary object of the present invention to provide apparatus according to which it becomes possible to avoid the above drawbacks encountered with conventional apparatus.

A more specific object of the present invention is to provide apparatus according to which it becomes possible to handle a sample and reagent preliminarily in such a way that before they are mixed together their temperature can be precisely determined and then the reagent and sample can be mixed together in a colorimetric cell to provide the possibility of measuring the absorption of light of a given wavelength by a component of the reagent the concentration of which diminishes as the reaction goes forward.

A further object of the present invention is to provide for purposes as set forth above containers for the sample and reagent which are constructed in such a way that the above procedures can be very conveniently carried out in connection with a colorimetric cell.

Moreover, it is an object of the present invention to provide apparatus which is particularly suited for measuring enzyme activity as set forth above.

Thus, the present invention involves measuring a property of a given sample which when mixed at a given temperature with a given reagent will produce a reaction wherein the concentration of a component of the reagent will diminish at a given rate, with this component being capable of absorbing light of a given wavelength to an extent determined by the concentration of the component, so that by directing the light of the given wavelength through the mixture of the sample and reagent while the reaction goes forward it is possible to determine the rate at which the concentration of this component diminishes and thus determine the property of the sample. Predetermined amounts of the sample and reagent are initially situated respectively in a pair of containers which respectively have open tops and one of which can be introduced into the other while the open tops remain directed upwardly and with the inner container when introduced into the outer container extending above the level of the contents in the outer container so as to prevent mixing of the contents of both containers while the inner container remains within the outer container with the open tops of both containers directed upwardly. After the sample and reagent are thus respectively situated in predetermined quantities in the inner and outer containers and after the inner container is sutated within the outer container, a colorimetric cell is connected in a fluid-tight manner to the open top of the outer container with the cell being in an inverted position and having its hollow interior communicating with the hollow interiors of both containers. With the assembly in this latter condition, the entire assembly together with the contents of the containers are brought to a given temperature. Then the entire assembly is inverted so that the contents of both containers discharge into the cell to mix therein and start the reaction at the given temperature. Immediately thereafter, when the reaction has started, the cell is situated in an instrument such as a photoelectric colorimeter or a spectrophotometer, for directing light of the above given wavelength through the cell so that it becomes possible to measure the rate at which the light of the given wavelength is absorbed by the component of the reagent whose concentration diminishes at a predetermined rate, so that in this way it becomes possible to measure the property of the sample.

Thus, the apparatus of the invention includes the above outer container which has an open top as well as an inner container which also has an open top and which is small enough to be received entirely within the outer container with both of the open tops directed upwardly and with the open top of the inner container situated substantially below the open top of the outer container. A tubular colorimeter cell which has opposed ends one of which is closed and the other of which is open is connected at its open end by way of a tubular connecting means, having opposed open ends, to the open top of the outer container with the tubular colorimetric cell communicating through its open end and through the connecting means with the interiors of both containers. Thus, by respectively situating a sample and reagent in the interiors of the above containers it is possible to provide an assembly as set forth above, to bring the assembly to the required temperature, and then to invert the assembly to carry out in the colorimeter cell the reaction wherein light of a suitable wavelength will be absorbed by a component of the reagent in a manner which will indicate the desired property.

BRIEF DESCRIPTION OF DRAWINGS

The invention is illustrated by way of example in the accompanying drawings which form part of this application and in which:

FIG. 1 is an exploded sectional elevation of one possible embodiment of components according to the present invention which can be assembled together to bring about the results of the invention;

FIG. 2 is a bottom end view of a connecting means which is illustrated in FIG. 1;

FIG. 3 is a top end view of the same connecting means;

FIG. 4 is a sectional elevation of containers shown in FIG. 1 assembled together and illustrated in a tilted condition;

FIG. 5 shows the assembly of the components of FIG. 1 situated in a schematically illustrated temperature-regulating means;

FIGS. 6A–6E respectively illustrate successive stages of use of the apparatus of the invention; and FIG. 7 is a perspective illustration of another embodiment of a connecting means according to the invention.

DESCRIPTION OF THE PREFERRED EMBODIMENTS

Referring now to the drawings, there is illustrated therein apparatus of the invention according to which it becomes possible to carry out measurements conforming to the principles of enzyme activity measuring and capable of providing highly accurate measurements.

Referring to FIG. 1, there is illustrated at the lower part thereof a relatively small reagent bottle 1 forming a container which has an open top 2. This container 1 which is shown in FIG. 1 is adapted to form an outer container and is adapted to contain a previously accurately measured enzyme activity measuring reagent solution consisting of the above substrate, coenzyme, pH adjusting reagent, etc. The reagent container 1 has a flat bottom and its open top 2 is situated at the upper end of a neck which is joined to the remainder of the container 1 by way of a shoulder 3. Thus, below the shoulder 3 the container 1 has a larger diameter than the diameter of the neck which terminates in the top open end 2 of the container 1. The open top 2 of the container 1 is capable of being tightly closed by way of a suitable rubber stopper or the like.

FIG. 1 illustrates just above the outer container 1 an inner container 4 which also has an open top and which is smaller than the container 1 so that it can conveniently be introduced into the latter. This inner container 4 is adapted to contain a previously accurately measured sample which is to be examined, such as serum, for example. The sample container 4 has a flat bottom 5 and is constructed in such a way that it can be introduced into the reagent container 1 and stand upright therein, the container 4 assuming at this time the position illustrated in dot-dash lines at 4' in FIG. 1.

A tubular connecting means 6, shown above the inner container 4 in FIG. 1, is provided for the purpose of removably interconnecting the outer container 1 with a colorimetric cell 11 which is shown in inverted condition in FIG. 1. This tubular connecting means 6 is made of rubber such as silicone rubber, neoprene rubber, etc., and it is formed with an interior tubular passage 7 while having opposed open ends. The intermediate connecting means 6 is provided at its exterior between its opposed ends with an outwardly directed flange 10. As is apparent from FIG. 2, the tubular portion 8 of the connecting means 6, which extends downwardly from the intermediate flange 10 thereof, is of a circular cross section both at the hollow interior portion thereof as well as at the exterior surface thereof. The size of the tubular portion 8 is such that it will form a tight closure at the upper neck of the container 1 when introduced into the neck of the container 1.

As is apparent from FIG. 3, the tubular portion 9 of the connecting means 6, which extends upwardly from the flange 10 thereof as viewed in FIG. 1, is of a circular cross section at its hollow interior tubular portion 7 but is of a square or polygonal cross section at its exterior. This exterior cross section matches the interior cross section of the colorimetric cell 11. This upper tubular portion 9 of the connecting means 6 is adapted to be forced with a tight fit through the open end 12A of the cell 11 into the latter to form a fluid-tight connection therewith.

The colorimetric cell 11 is of course of a cross section matching the cross section of the exterior surface of the tubular portion 9, and this tubular cell 11 has opposed ends one of which is closed and one of which is open. The cell 11 is shown in FIG. 1 in an inverted condition where its open end 12A is directed downwardly while its closed end is situated at the top. The cell 11 is generally made of a light-transmitting material such as quartz, glass, etc. It is also possible to make this cell 11 of a high molecule material such as polystyrene, polyolefin, etc. Of course, while the configuration of the cell 11 and the tubular portion 9 is square of prismatic in cross section in the illustrated example, it is also possible to make the cell 11 as well as the portion 9 of connecting means 6 of a circular cylindrical configuration. Thus if the cell 11 is of a circular cross section then of course the tubular portion 9 will be of a corresponding circular cross section.

FIg. 4 illustrates the assembly of the outer container 1 and the inner container 4 in a tilted attitude where the open tops of these containers are directed downwardly toward the left. If the container 1 is inverted to such an extent that the open top 2 thereof is directed straight down, then it is possible for the container 4 to fall out of the container 1. In fact it is possible easily to remove the container 4 from the container 1 by such a procedure. However if the container 1 and the container 4 are inverted only to an extent such as that shown in FIG. 4, so that the open top of the container 1 does not assume an attitude where it is directed straight down, then in the oblique attitude such as that shown in FIG. 4 the interior container 4 will engage the shoulder 3 so that it will not slip out of the container 1 when the operator desires to discharge the contents of the containers 1 and 4 without causing the container 4 to slip out of the container 1.

FIG. 5 illustrates the entire assembly of FIG. 1 shown in the assembled condition with the enzyme activity measurement reagent solution 12 situated in the outer container 1 and the sample 13 which is to be measured situtated in the inner container 4. It will be seen that after the liquid sample 13 is situated in the inner container 4 the latter may be carefully dropped into the outer container 1 in such a way that the container 4 will extend above the contents 12 of the container 1 preventing the contents 12 from mixing with the sample 13 while the parts have the position shown in FIG. 5. With the inner container 4 thus situated within the outer container 1 and with the latter assembled with the cell 11 by way of the connecting means 6, as shown in FIG. 5, the entire assembly is capable of being situated as a single unit in an opening 15 in a heating block 14 of a temperature-regulating means of a known construction capable of operating in such a way that the temperature prevailing in the opening 15 will be transmitted throughout the entire assembly and the contents 12 and 13 of the containers 1 and 4, respectively. As is apparent from FIG. 5, because the container 4 extends above the level of the contents 12 of the container 1, this container 4 serves to maintain the reagent solution 12 separate from the liquid sample 13 which is to be examined. Thus while the solution 12 and liquid sample 13 are in a state of good heat transmission so that any temperature differential therebetween will disappear very rapidly, at the same time, they are reliably maintained separate from each other. Thus, while the parts are in the condition shown in FIG. 5 it cannot happen that the enzyme activity measurement reagent solution 12 and the liquid sample 13 which is to be examined can be mixed together so as to produce the enzyme reaction. Thus, in a relatively short time the reagent container 1 and all of the other components situated within the opening 15 will reach the temperature which is determined by the finely regulated temperature control system acting on the heating block 14, so that a state of thermal equilibrium is rapidly achieved. It is apparent that at this time the reagent container 1 as well as all of the other components not only are mechanically but also are thermally in the state of a single body. It is possible to achieve the same results by utilizing a water bath for heat regulation instead of a heating block 14.

The manner in which the above-described structure of the invention is utilized is illustrated in FIGS. 6A–6E. The particular example utilized to illustrate the invention involves enzyme activity measurement, and the method is illustrated up to the time when the enzyme activity measurement is started.

Referring to FIG. 6A, it will be seen that a sample 13 which is to be examined is accurately measured by way of a pipette 16 and is then situated within the inner container 4. Then the enzyme activity measurement reagent solution 12 is accurately measured by way of a pipette 17 and is situated within the outer container 1. It is to be noted that it is also possible to utilize a reagent which is in a frozen-dry powder state. Such a reagent is accurately measured and introduced into the reagent container 1. To this latter accurately measured quantity of powder there is then added a predetermined volume of purified water so as to achieve in this way the enzyme activity measurement reagent solution 13. It is of course desirable that all of the instruments employed be in a clean and dry condition.

Referring now to FIG. 6B, it will be seen that after the sample and reagent are respectively situated in the inner and outer containers, the inner container is situated within the outer container so that these parts will then have the condition illustrated in FIG. 6B. The inner container 4 is introduced carefully through the open top end of the outer container 1 and then permitted to drop downwardly into the contents 12 of the outer container 1, the flat bottoms of the inner and outer containers enabling them to have the position shown in FIG. 6B. Also it will be noted that the volume of the contents 12 and the length of the inner container 4 are such that the inner container 4 will extend above the level of the contents 12 of the outer container 1.

As is indicated in FIG. 6C, subsequent to the procedures described above in connection with FIG. 6B, the connecting means 6 has its cylindrical portion 8 introduced into the outer container 1 while the portion 9, which of course is of a square cross section, for example, matching that of the colorimetric cell 11, is introduced into the lower open end of the cell 11, so that the assembly shown in FIG. 6C will be provided. The tubular portions 8 and 9 respectively projecting in opposite directions from the flange 10 of the connecting means 6 are respectively pressed into the open top of the container 1 and the lower open end 12A of the cell 11 until the container 1 and the cell 11 engage the opposed faces of the flange 10. Thus, the fluid-tight connection is achieved not only by engagement of the inner surface portions of the cell 11 and container 1 with the exterior surface portions of the connecting means 6, but also by pressing of the ends of the container 1 and cell 6 against the opposed faces of the flange 10.

With an assembly thus provided as shown in FIG. 6C, this assembly is then introduced into the opening 15 of the temperature-regulating means 14. Thus the heating block 14 will create in the opening 15 a temperature by means of which all of the assembly shown in FIG. 6D will be brought to the required temperature in a uniform manner as well as in a rapid manner. It will be noted that the closed end of the cell 11 extends somewhat above the heating block 14 so that the operator can conveniently introduce the assembly into and remove it from the opening 15. Thus, all of the assembled elements will rapidly reach thermal equilibrium. The internal diameter of the opening 15 is such as to correspond to the outer diameter of the outer container 1, and the depth of the opening 15 is such as to permit almost the entire assembly to be received in the opening 15, without detracting from the convenience with which the assembly can be introduced into and removed from the opening 15.

After a sufficient time has elapsed for achievement of thermal equilibrium of all of the elements shown in FIG. 6D, the entire assembly is removed from the opening 15 and is then turned over several times for thoroughly mixing the sample and reagent. When the assembly is inverted, the enzyme activity measurement reagent solution 12 and the liquid sample 13 which is to be examined discharge downwardly out of the containers 1 and 4, respectively, flow through the interior 7 of the tubular connecting means 6, and enter the interior of the colorimetric cell 11 where the sample and reagent mix with each other. Thus, the enzyme reaction is started. The operations in connection with turning the entire assembly over several times requires an extremely short interval, so that the enzyme reaction which occurs during this extremely short interval has no influence upon the measurement. Moreover, it will be noted that during this turning of the assembly and mixing of the sample and reagent the liquid contents within the assembly is closed off from the outer atmosphere. At the same time, loss of heat is only minimal during the extremely short interval when the sample and reagent are mixed as set forth above, so that the loss of heat is extremely small and the temperature of the entire system which has been achieved at the temperature-regulating means 14 hardly changes.

Now the entire assembly is maintained in an inverted condition as compared with the condition thereof shown in FIGS. 6C and 6D, so that the liquid contents of containers 1 and 4 will now remain in the cell 11 in a completely mixed condition, whereupon the cell 11 can be removed (FIG. 6E) easily from the connecting means 6, simply by being slipped off the latter, and immediately the cell 11 is situated in an instrument such as a photoelectric colorimeter or a spectrophotometer, to enable the measurement of the rate of variation of absorbance to be carried out while the temperature remains at the value achieved by way of the temperature-regulating means 14.

Thus, the enzyme reaction promptly enters into the rate-determining stage where conditions of complete mixture and thermal equilibrium of the entire system have been established. Therefore, with the apparatus of the present invention, the measurement of the rate of variation of absorbance can be immediately carried out. In measuring enzyme activity, the initial reaction speed is regarded as representing the true value. With the apparatus of the invention it has been found that the true value of the measurement of enzyme activity obtained during the initial reaction speed is highly accurate.

As is apparent from the above description the present invention is particularly effective for achieving enzyme activity measurement. While the details of the above-described features of the invention can vary considerably, the important points to be taken into consideration with respect to these details and some examples of these details are indicated below.

Thus, with respect to heat transmissivity, it is desirable to make the outer container 1 of glass rather than plastic. If plastic is utilized, it is preferable that the wall thickness of the plastic be less than one-fourth that of a corresponding glass container. Also, with respect to heat transmissivity and also in connection with specific gravity, it is highly desirable that the inner container 4 be made of glass. If the inner container 4 is made of plastic which has a low specific gravity, when the container 4 is introduced into the reagent solution 12 within the outer container, the container 4 may not sink in the desired manner directly to the bottom of the outer container and instead may as a result of effects of buoyancy tilt undesirably before reaching the bottom of the container 1. For similar reasons it is preferable that the dimensions and capacity of the outer container 1 and the inner container 4 be determined in accordance with the most suitable values when taking into consideration the volumes of the liquids which are to be handled. The internal diameter of the inner container 4 and of the tubular passage 7 of the connecting means 6 must be of such a value that liquid can pass freely through the interiors of the inner container 4 and the connecting means 6. Moreover, it will be seen that the exterior diameter of the inner container 4 is at least as great as the internal diameter of the tubular passage 7, so that the inner container 4 cannot be received in or travel through the tubular passage 7. In the event that these internal diameters are less than 8 millimeters, then the flowing in and flowing out of the liquid materials may present some difficulties because of viscosity of the liquid. It is preferred, therefore, that the interior diameters of the inner container 4 and the tubular passage 7 of the connecting means 6 be at least 8 millimeters.

A further feature of the invention resides in providing a connecting means 6 which instead of having a tubular portion 8 as described above to be received in the upper part of the outer container 1 has a tubular portion 8 as illustrated in FIG. 7. Referring to FIG. 7, it will be seen that a plurality of notches 16, 16', 16'', and 16''' are formed in the tubular portion 8 extending from the free end thereof toward but terminating at a suitable distance from the flange 10. These notches are preferably angularly distributed about the axis of the connecting means 6 through 90° so that between these notches there are defined a number of tongues as illustrated in FIG. 7. As is apparent from FIG. 6E, for example, when the connecting means of FIG. 7 is placed in the outer container 1, the free ends of the tongues will extend freely into the container 1 somewhat beyond the shoulder 3 thereof. As a result, when the assembly is inverted as described above, it will not be possible for the inner container 4 to slide with respect to the shoulder 3 into a position where the container 4 will itself block the flow of the liquid contents down through the tubular passage 7 of the connecting means 6. With a construction as shown in FIG. 7, part of the inner container 4 will be received in one of the notches so that a precise alignment of the inner container 4 with the connecting means 6 will be reliably avoided and a reliable flow of the liquid contents into the colorimetric cell 11 will be assured.

With respect to the colorimetric cell 11, it is preferred to make the latter of a material which has a high degree of heat insulation, or in other words of a material which has an extremely low coefficient of thermal conductivity. At the same time, the required light transmissivity of the cell 11 must be maintained. It is possible to use a material such as polystyrene which will fulfill both of these requirements.

Because it is possible by way of the present invention to maintain the mixed reagent and sample and the cell 11 during measurement of the initial reaction speed in a fully adequate manner at the predetermined temperature achieved initially by way of the temperature-regulating means 14, it becomes possible to utilize for measurement purposes a photoelectric colorimeter or the like whose light-measurement section is not temperature controlled.

It is apparent, therefore, that the enzyme activity measuring apparatus according to the present invention is highly advantageous in practical use.

What is claimed is:

1. In an apparatus for determining a property of a given sample, an outer container having an open top, an inner container also having an open top and being small enough to be received entirely within the outer container with both of said open tops directed upwardly and with the open top of said inner container being situated substantially below the open top of said outer container, a tubular colorimetric cell having opposed ends one of which is closed and the other of which is open, and tubular connecting means having opposed open ends and an unobstructed, completely open internal tubular passage extending from one to the other of said open ends and having an internal cross sectional area which is too small to receive said inner container, said tubular connecting means being removably connected with said open top of said outer container and said open end of said cell for fluid-tightly connecting said cell to said outer container with the interior of said cell communicating with the interiors of said containers so that when a sample and reagent are respectively situated in the interiors of said containers in an amount according to which the inner container when situated within the outer container will extend above the level of the contents of said outer container, said connecting means can fluid-tightly connect said cell to said outer container to enable both containers and said cell to be inverted as a unit for discharging the contents of both containers into said cell to mix therein and provide a reaction according to which a property of said sample may be measured in an instrument.

2. The combination of claim 1 and wherein both of said containers have flat bottoms.

3. The combination of claim 1 and wherein said outer container has a neck terminating in said open top of said outer container and a shoulder connecting said neck to the remainder of said outer container which is of a greater diameter than said neck, said inner container being of a diameter smaller than said neck and of a length smaller than the distance from said shoulder to the bottom of said outer container, so that said inner container will engage said shoulder when the containers are tilted with the inner container situated within the outer container.

4. The combination of claim 1 and wherein said connecting means has between its ends an outer flange to be situated between the open top of said outer container and the open end of said cell, said connecting means having a pair of tubular portions respectively extending from said flange along the interiors of said outer container and cell.

5. The combination of claim 4 and wherein said inner container and said tubular connecting means both have an inner diameter of at least 8 millimeters.

6. The combination of claim 4 and wherein said connecting means is formed with a plurality of notches extending axially along said connecting means from the end thereof which is distant from said flange and which is received in said outer container, with the latter end of said connecting means being engaged by said inner container when both of said containers are inverted, whereby between said notches said connecting means has tongues for engaging said inner container to prevent the latter from blocking the flow of the contents of said containers through said connecting means into said cell.

7. The combination of claim 1 and wherein both of said containers are made of glass.

8. The combination of claim 1 and wherein said cell is made of a material which is capable of providing a high degree of heat insulation.

9. The combination of claim 8 and wherein said material is polystyrene.

10. The combination of claim 4 and wherein said connecting means is made of rubber.

11. The combination of claim 1 and wherein a temperature-regulating means is formed with an opening for receiving the assembly of said containers, connecting means, and cell to bring the entire assembly including the contents of said containers to a given temperature.

12. The combination of claim 11 and wherein the depth of said opening is such that when the assembly is received therein said cell will project outwardly beyond said opening at the region of the closed end of said cell to facilitate introduction of the assembly into and removal thereof from the opening of said temperature-regulating means.

13. The combination of claim 1 and wherein said tubular connecting means is made of a yieldable elastic material for frictionally engaging said outer container and cell to provide the fluid-tight connection therebetween.

14. The combination of claim 13 and wherein said material is rubber.

15. The combination of claim 13 and wherein said connecting means has between its ends an outer flange situated between and engaging ends of said cell and outer container for at least contributing to the fluid-tight connection therebetween by engagement between said flange and said ends of said cell and outer container.

* * * * *